United States Patent [19]

Kampff

[11] Patent Number: 4,493,712
[45] Date of Patent: Jan. 15, 1985

[54] FOOT SOAKER AND RESTER

[76] Inventor: Ronald J. Kampff, 3033 Toledo Ave. S., St. Louis Park, Minn. 55416

[21] Appl. No.: 424,895

[22] Filed: Sep. 28, 1982

[51] Int. Cl.³ .............................................. A61F 7/00
[52] U.S. Cl. ....................................... 604/293; 4/574
[58] Field of Search ............... 128/253, 399, 400, 402; 604/293, 289, 19; 4/574

[56] References Cited

U.S. PATENT DOCUMENTS

| 1,715,043 | 5/1929 | Oye | 128/25 B |
|---|---|---|---|
| 2,025,936 | 12/1935 | Clearman | 604/293 |
| 2,594,024 | 4/1952 | Hyde | 604/293 |
| 2,709,435 | 5/1955 | Kress | 604/293 |
| 2,736,038 | 2/1956 | Mansfield | 604/293 |

FOREIGN PATENT DOCUMENTS

| 290987 | 7/1914 | Fed. Rep. of Germany | 604/293 |
|---|---|---|---|
| 1290721 | 9/1972 | United Kingdom | 4/574 |

Primary Examiner—John D. Yasko
Attorney, Agent, or Firm—Thomas A. Lennon

[57] ABSTRACT

A device particularly useful for persons having circulatory problems such as diabetics comprising a liquid confining section in which a person's foot can be soaked and a leg and foot supporting section which comfortably supports the leg and foot and maintains said foot in a generally upright position.

7 Claims, 7 Drawing Figures

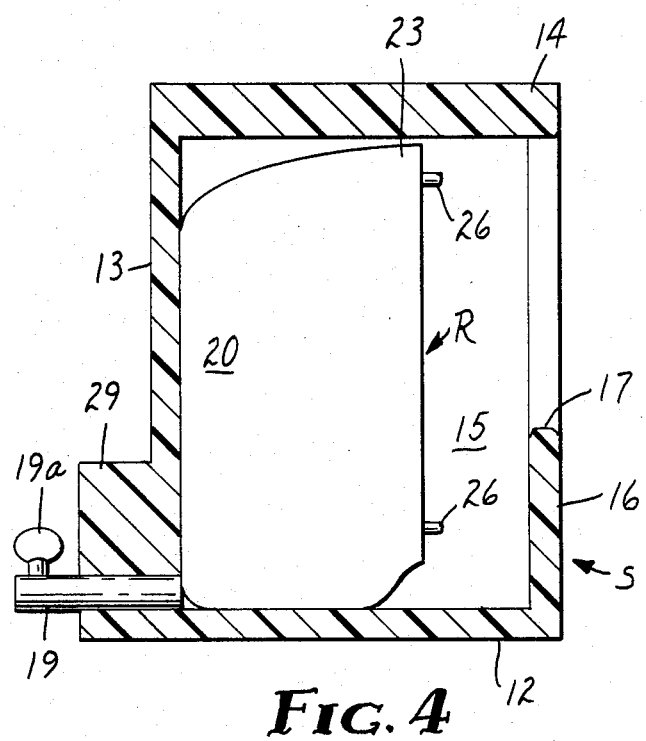
FIG. 4
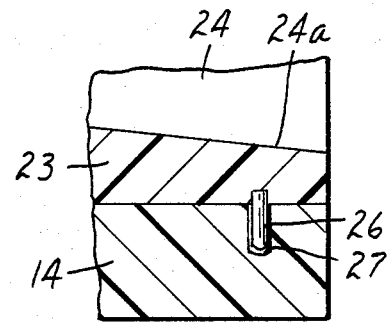
FIG. 5
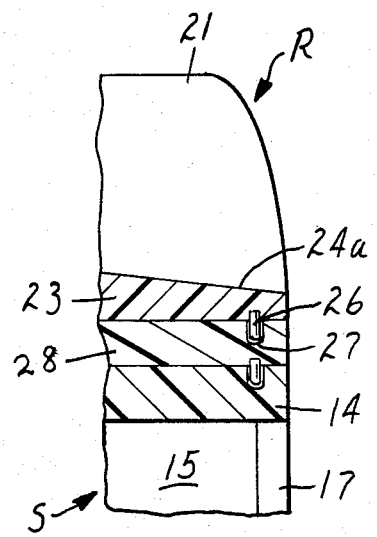
FIG. 7
FIG. 6

FOOT SOAKER AND RESTER

Persons such as diabetics whose blood circulates with difficulty, particularly in extremities such as their legs, have problems when it is necessary for them to soak their feet. When soaking their feet, it is important that the leg and foot not being soaked be in an elevated position, to improve the circulation and reduce the pumping strain on the heart. In addition, substantial pain and discomfort is experienced by such a person if the leg twists substantially or suddenly falls from an elevated position.

Therefore, an object of this invention is to provide a device which enables a person to soak one foot while resting the other foot in a comfortable elevated position.

Another important object is to provide a device for soaking the foot which maintains the foot not being soaked in an elevated confined condition in which the foot is prevented from turning, twisting or falling inadvertently.

Still another object is to provide a foot soaking device which permits the foot to be installed in or withdrawn from the liquid both with a minimum of physical effort.

Still another object is to provide a foot soaking device which enables both feet to be comfortably supported in an elevated non-twisting condition when the soaking has been completed.

Still another object is to provide a foot soaker which also provides a rest for the other foot which is secured against turning and which is conveniently positioned for drying with a towel by another person.

These and other objects and advantages will be readily apparent from a review of the attached drawings and a reading of the following description which relates to said drawings, and in which drawings:

FIG. 4 is a side elevational view with portions broken away showing one preferred form of invention in which the foot rest is capable of being stored inside the soaker.

FIG. 5 is a partial sectional view on an enlarged scale through the foot rest and foot soaker showing how the foot rest and foot soaker are removably connected in operative position.

FIG. 6 is a perspective view of an insert used to selectively increase the height of the foot rest.

FIG. 7 is a sectional view on an enlarged scale through a portion of the soaker, insert and rest showing them removably fastened together in operative position.

Figure 1:
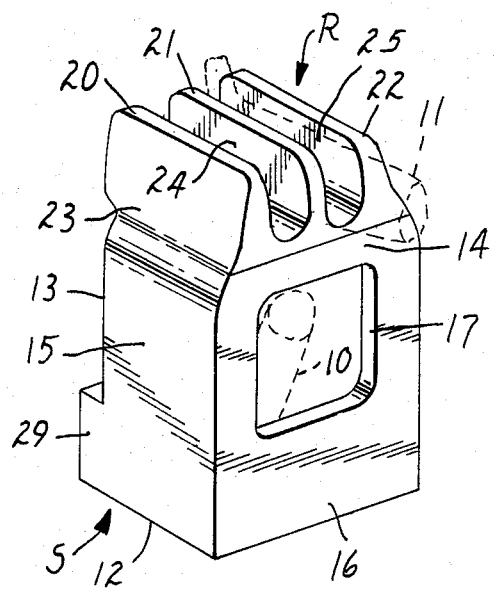
FIG. 1 is a perspective view of one preferred embodiment of this invention showing one leg with it's foot soaking in the bath and the other leg in an elevated position with it's foot resting in a confined non-twistable position.
Figure 2:
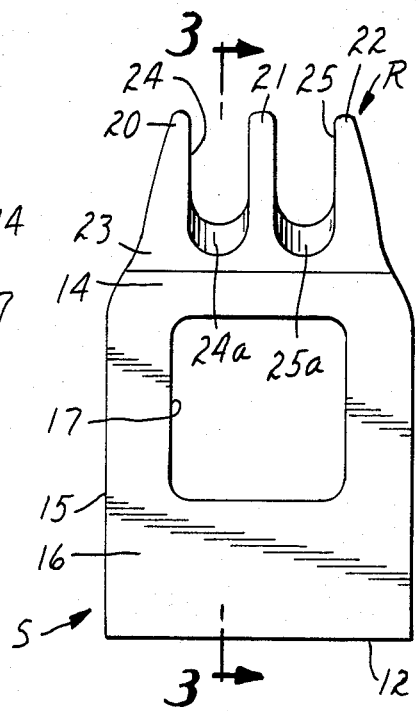
FIG. 2 is a front elevational view of the soaking device of FIG. 1.
Figure 3:
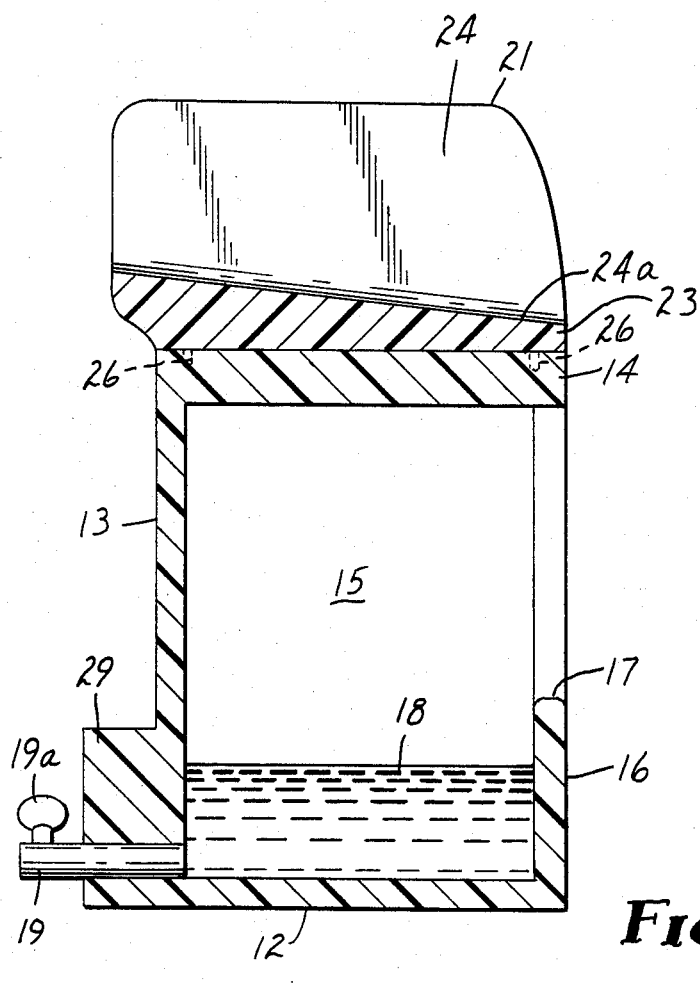
FIG. 3 is vertical longitudinal sectional view thereof taken along the line 3—3 of FIG. 2.

Referring to the drawings, and initially to FIG. 1, a preferred embodiment is shown having a soaking section indicated generally by the letter S and a resting section indicated generally by the letter R and which is shown in perspective, with a person's left leg 10 shown in broken outline in the bath and said person's right leg 11 shown in broken outline installed in the rest section R.

Each of the sections S and R are preferrably formed of strong, lightweight waterproof material such as styrofoam or plastic, and are preferably of unitary construction.

The soaking section S has a bottom floor 12, a back wall 13, a top wall or roof 14, identical side walls 15, and a front wall 16 having an opening 17 formed therein to permit a foot to be inserted into the interior and removed therefrom.

The top edge 16a of the lower front wall must be high enough to confine an adequate amount of liquid 18, usually water, within the soaker so that it will cover the entire foot when it is put therein, said edge 16a defining the maximum amount of liquid which can be confined therein.

To permit drainage of the liquid, a drain pipe 19 with a spigot 19a is installed in the back wall 13 at the floor level so that all the liquid can be removed therefrom.

The soaker also has an anti-tipping part 30 that is a ledge which extends rearwardly beyond the rear wall 13 across the entire width of the soaker, so that a part of the drain pipe is actually installed in ledge 30, the bottom of ledge 30 being flush with the bottom outer surface of bottom wall 12. This ledge or bar 30 gives the unit additional stability with the use of a minimum of material.

Mounted atop the soaking section S is the rest section R. Said section R includes elongate parallel spaced apart ribs 20, 21, and 22 connected by a base 23, and defining therebetween feet receiving grooves, troughs or channels 24 and 25. Trough 24 is designed to receive the left foot and trough 25 is designed to receive the right foot. The bases 24a and 25a of each trough are inclined downwardly from back to front so as to more comfortably accommodate the underside of the foot, ankle and leg portions seated therein, since the legs will normally be inclined upwardly during use.

In referring to the front to back inclination or slanting of the bottoms of the leg supporting troughs, the front is considered to be the side or end facing the user and closest to him and the back side or end is the side or end furtherest away from the user, with the assumption that the user is positioned, presumably in a seated condition on the side of the soaker facing the front opening 17 and front wall 16.

The inclination of the upwardly facing leg and foot engaging portions of the troughs enables the legs and feet to be held in a comfortable upwardly and forwardly inclined condition and also enables any liquid from the leg or feet to drain away quickly without collecting in pools or puddles in the foot rest.

The distance between the ribs 20 and 21 and between 21 and 22 is such as to allow the feet to slip easily in and out thereof, and yet holds them in a generally upright position.

It will also be noted that the inner side walls of the troughs taper gradually inwardly, terminating in an upwardly facing concavely curved bottom which comfortably receives the heel of the foot and the calf of the leg, and which is somewhat narrower than the top of the trough, the wider trough top facilitating the entry of the leg and foot into the trough.

The troughs are also deep enough so the sides of the feet connot move very far before they engage the sides of the trough and are prevented by said walls from moving any further. Thus, the troughs hold the feet generally upright and prevent any significant twisting or turning thereof.

This non-twisting of the feet is important not only to diabetics, but also to people who have limited or no use of their legs due to birth defects, injury or illness such as polio.

As illustrated, the rest R is removably mounted atop soaker S by means of four depending pins or legs 26 which removably seat in upwardly facing openings 27 formed in the top wall 14 of the soaker.

Thus, in use, liquid is put into the soaker S and a foot is installed therein. The other foot is put in one of the troughs of the foot rest and held against turning movement.

When one foot has been soaked enough, it is removed from the soaker and put in the foot rest and the other foot which was on the foot rest R is put into the soaker.

When the user is finished, the liquid can be conveniently drained from the bath by means of the drain 19 without having to carry the entire unit full of liquid to a sink, floor drain, toilet or other drainage facility.

If the user needs some additional height, the insert 28 is provided which has four depending legs 26' identical to the pins 26 on the foot rest and positioned the same distance apart so that they can seat in the holes 27 in the top of the soaker to hold the insert in place.

The insert itself has holes or openings 27' in the top thereof identical to the holes 27 in the soaker so that the pins 26 of the rest can seat in the insert openings 27' and hold the rest in operative position atop the insert 28.

In one preferred form of the invention, the rest R and soaker S are dimensioned and designed to that the foot rest can be stored inside the soaker, as illustrated in FIG. 4, thereby reducing the amount of space necessary to store the unit when not in use.

The unit will be most frequently designed so that it will normally be used by someone seated in a conventional chair, the seat of which is approximately 19" from the floor, or some other body support of comparable height. However, it is apparent that the device of this invention can be made in other sizes to cope with body supports having heights different than the conventional chair.

It will also be noted that the foot rest unit R can be used independently of the soaker S as a foot rest, and can be placed on the floor or on some other support, which might even be an elevated support, particularly if the user wants a comfortable foot rest which comfortably supports his feet and legs, without necessarily using it in conjunction with a foot soaking operation.

In one preferred form of the invention, the width of the soaker is approximately 2 feet and the overall height of the device with the rest mounted atop the soaker is in the range of 3½ to 4 feet.

For persons who do not have circulatory or other leg problems requiring holding of the feet upright, and do not necessarily need the upwards inclination of the legs when resting, the top wall 14 of the soaker section S can also be used as a foot rest without the foot rest R being mounted thereon.

The dimensions are such that the legs of the user when in the foot rest R are at least slightly upwardly inclined.

It will, of course, be understood that various changes may be made in the various parts and dimensions referred to and illustrated herein, without departing from the scope of this invention.

I claim:

1. A device comprising a first part adapted to receive a foot of a human and hold enough liquid to cover said foot, and a second part adapted to support the other foot of said human in a generally upright position of limited turning movement while said first named foot is in the liquid housed by said first part,
    wherein said parts are separable, and means for maintaining said parts in connected spaced apart relationship,
    and wherein said first part has an upwardly facing top surface and said second part has a downwardly facing bottom surface opposing said top surface and adapted to engage and be supported by said top surface, and
    wherein said means for maintaining said parts in spaced apart relationship comprises spacer means insertable between said parts and adapted to engage said top and bottom surfaces whereby said spacer means is supported by said first part and supports said second part.

2. A device comprising a first part adapted to receive a foot of a human and hold enough liquid to cover said foot, and a second part adapted to support the other foot of said human in a generally upright position of limited turning movement while said first named foot is in the liquid housed by said first part,
    wherein said first part includes wall structure defining a hollow interior chamber capable of confining liquid therein, and
    said wall structure including a generally vertical front wall facing the user, and
    an opening in said front wall adapted to permit a human foot to pass therethrough into the interior.

3. The device of claim 2, wherein said second part is capable of passing through said opening in said front wall and being stored in said chamber.

4. The device of claim 1, wherein said spacing means has a top surface which opposes and engages the bottom surface of said second part and a bottom surface which oppose and engages the top surface of said first part,
    fastening means carried by said parts and spacing means adapted to prevent sliding movement between said opposing surfaces,
    said fastening means including first fastening means carried by the bottom surfaces of said second part and said spacing means and second fastening means carried by the top surfaces of said first part and said spacing means,
    said first and second spacing means being adapted to cooperatively engage each other and prevent said sliding movement between said opposing surfaces.

5. The device of claim 4, wherein one of said first and second fastening means is an elongate member and the other is a recess adapted to receive said elongate member.

6. A device comprising a first part adapted to receive a foot of a human and hold enough liquid to cover said foot, and a second part adapted to support the other foot of said human in a generally upright position of limited turning movement while said first named foot is in the liquid housed by said first part,
    wherein said second part is located above and supported by said first part, and
    wherein said second part includes a pair of spaced apart upstanding members,
    said members having substantially vertical surfaces facing one another and spaced apart to receive said foot therebetween,
    said surfaces maintaining said foot in a substantially vertical upright position and preventing any significant turning of said foot, wherein the spaces between said members have a proximal end closest to the user and a distal end most remote from the user, and said second part having a floor portion underlying said foot receiving spaces, and said floor portion being inclined upwardly from said proximal end to said distal end, and wherein said first part includes wall structure defining a hollow interior chamber capable of confining liquid therein, and said wall structure including a generally vertical front wall facing the user, and an opening in said front wall adapted to permit a human foot to pass therethrough into the interior.

7. The device of claim 6, wherein said second part has three spaced apart substantially laterally aligned upstanding members defining two foot receiving spaces therebetween, said members having substantially vertical surfaces facing one another and spaced apart to receive a foot therebetween, said surfaces maintaining said foot in a substantially vertical upright position and preventing any significant turning of said foot.

* * * * *